United States Patent [19]

Yacoubian et al.

[11] Patent Number: 5,683,405
[45] Date of Patent: Nov. 4, 1997

[54] VASCULAR OCCLUDER

[75] Inventors: Vahe S. Yacoubian, Glendale, Calif.; Douglas G. Fox, Sandy, Utah; John T.M. Wright; Donald P. Elliott, both of Denver, Colo.

[73] Assignee: Research Medical Inc., Midvale, Utah

[21] Appl. No.: 519,317

[22] Filed: Aug. 25, 1995

[51] Int. Cl.⁶ .................................................. A61B 17/00
[52] U.S. Cl. .................. 606/158; 606/151; 606/157; 606/221; 24/545; 24/547; 24/549; 600/218
[58] Field of Search .................... 606/158, 157, 606/151, 139, 221, 208, 207, 205, 210, 211; 227/902; 600/201, 217, 218; 24/530, 557, 545–549, 551–554

[56] References Cited

U.S. PATENT DOCUMENTS

| | | | |
|---|---|---|---|
| 552,111 | 12/1895 | Frye | 24/554 |
| 1,025,363 | 5/1912 | Benoy | 606/208 |
| 1,123,290 | 1/1915 | Von Herff | |
| 3,827,438 | 8/1974 | Kees, Jr. | |
| 3,868,957 | 3/1975 | Doddington | 606/158 |
| 4,360,023 | 11/1982 | Sugita et al. | |
| 4,444,187 | 4/1984 | Perlin | |
| 4,484,581 | 11/1984 | Martin et al. | |
| 4,658,822 | 4/1987 | Kees, Jr. | |
| 4,660,558 | 4/1987 | Kees, Jr. | |
| 4,724,838 | 2/1988 | Hasson | 606/207 |
| 4,765,335 | 8/1988 | Schmidt et al. | |
| 4,777,949 | 10/1988 | Perlin | |
| 4,777,950 | 10/1988 | Kees, Jr. | |
| 4,796,625 | 1/1989 | Kees, Jr. | |
| 4,943,298 | 7/1990 | Fujita et al. | |
| 4,961,743 | 10/1990 | Kees, Jr. et al. | |
| 5,053,045 | 10/1991 | Schmidt et al. | |
| 5,074,870 | 12/1991 | von Zeppelin | |
| 5,133,724 | 7/1992 | Wilson, Jr. et al. | 606/151 |
| 5,167,618 | 12/1992 | Kershner | 606/205 |
| 5,496,335 | 3/1996 | Thomason et al. | 606/205 |

FOREIGN PATENT DOCUMENTS

| | | | |
|---|---|---|---|
| 450896 | 4/1913 | France | 24/549 |
| 3722311 | 1/1989 | Germany | |
| 403242140 | 10/1991 | Japan | 606/205 |
| 1203337 | 8/1970 | United Kingdom | 24/557 |

OTHER PUBLICATIONS

Bunt et al.; "Iatrogenic Vascular Injury During Peripheral Revascularization"; Journal of Vascular Surgery; 1985; pp. 491–498.

Pabst et al.; "Reduced Intimal Injury to Canine Arteries with Controlled Application of Vessel Loops"; Journal of Surgical Research; Sep. 1989; pp. 235–241.

"Vascular Occluders"; In Vivo Metric Produc Bulletin; Mar. 1990; 5 pages.

"Instruments that Save"; Applied Vascular Cross–Reference Guide; Jan. 1991; 1 page (double sided).

Sentinel Loops Silicone Vascular Tapes/Vascular Tourniquet Kits; Argyle; 1 page.

"Small Clips, Big Value"; Applied Vascular; 1993; 2 pages.

Primary Examiner—Jeffrey A. Schmidt
Attorney, Agent, or Firm—Trask, Britt & Rossa

[57] ABSTRACT

A vascular occluder clip including a resiliently-biased pair of clamping elements extending transversely to longitudinally-extending members. Gripping loops or pads are provided for grasping by the user and compression of the members against the biasing force to separate the clamping elements. The gripping loops or pads extend from the longitudinal members on the opposite side thereof from the clamping elements.

23 Claims, 3 Drawing Sheets

VASCULAR OCCLUDER

BACKGROUND OF THE INVENTION

1. Field of the Invention

The present invention relates generally to occlusion of blood vessels, and more specifically to an external coronary artery occluder also having general application to occlusion of other vessels for management of the surgical field.

2. State of the Art

Medical science has addressed the need for occlusion of blood vessels during surgical procedures for centuries, and the manner in which occlusion has been effected in the prior art has seemingly been limited only by the imagination of the practitioner. Both internal and external vascular occluders of various configurations are well known in the art, and perform the occlusion function with various degrees of efficiency and effectiveness.

Injury and potential injury to the patient in the course of vascular occlusion has been a cause of some concern and the subject of investigation, particularly in more recent years as discussed in Bunt et at, "Iatrogenic vascular injury during peripheral vascularization", *Journal of Vascular Surgery* 1985; 2:491–8, and Pabst et al, "Reduced Intimal Injury to Canine Arteries with Controlled Application of Vessel Loops", *Journal of Surgical Research* 47, 235–241 (1989).

It is particularly desirable to create a dry (assanguineous) field while performing the coronary anastomosis during continuous retrograde warm cardioplegia, although this is obviously a desired result during any type of intermittent or continuous antegrade or retrograde cardioplegia. A relatively bloodless field facilitates visualization by the surgeon, thus making the performance of the anastomosis less cumbersome. Intraluminal occluders are known in the art, but the insertion of any foreign body intraluminally is obviously to be avoided if possible. A carbon dioxide blower has been used for creating a dry field; however, this gas can make the endothelium dryer and is probably traumatic. Using a fine suction tip to suction the coronary artery is also possible, but such action will often inadvertently injure the intima by repeated touching with the suction tip, a notably undesirable result.

Positive external vascular occlusion has been effected using a number of different prior art devices, many of which are discussed in the aforementioned Bunt et al review. Among the more widely used prior art devices in current surgical practice are constrictable loop tourniquets and inflatable external cuffs, both of which surround the vessel in use and thus require surgical exposure of the blood vessel, and various types of spring-loaded clips and clamps, one of the more popular of such devices being the so-called "bulldog" clip. The "bulldog" clips, exemplified by the ATRAUMAX lines of surgical spring clips offered by Applied Vascular Devices, Inc. of Laguna Hills, Calif., employ two parallel, blunt-ended plastic jaws which are coil spring-biased toward each other and which maintain their parallel relationship during the range of movement from the open to the closed position. A cushioning material may be applied to the interior of the jaws in some embodiments in an attempt to alleviate trauma to the vessel being occluded, although testing has shown that the spring force employed in these clips is generally sufficient to cause injury to the occluded vessel even in the presence of such cushioning. Furthermore, the bulk of the bulldog clip and in particular of the jaws, with or without associated cushioning material, renders it difficult to apply that clip to the coronary artery embedded in the fat pad on the face of the heart without surgically exposing the vessel.

SUMMARY OF THE INVENTION

In contrast to the prior art, the present invention provides an external vascular occluder of simple but elegant design and robust construction, applicable in an atraumatic manner to a vessel such as the coronary artery and free of any requirement for pre-application surgical exposure of the vessel.

A preferred embodiment of the invention comprises a unitary resilient clip structure of stainless steel wire, folded and bent to define two horizontally-extending gripping loops, each loop including a first and a second leg extending distally from a proximally-located bight. The two legs of each loop converge distally at an acute angle, overlapping to close the distal end of each loop. The two loops are divergent in a proximal direction, and lie in slightly off-vertical planes which diverge from bottom to top. The first, lower and inner legs of the loops extend distally in substantially the same horizontal plane after crossing the second, outer legs and lie in substantially parallel relationship before turning inwardly in that plane and then downwardly in parallel at a substantially perpendicular orientation to the horizontal plane. The downwardly-oriented portions of the first legs comprise vessel clamping elements, and terminate in trocar points. The downwardly-extending portions may be bowed slightly outwardly, to better accommodate and grip a clamped vessel. The second, upper and outer legs of each loop are bent upwardly with respect to the plane of the horizontally parallel first legs after crossing the first, lower legs to close the loops. These upwardly-extending leg portions are bent over inwardly and then downwardly to form yokes enveloping first legs of the same loop extending therethrough. At the inner, lower extent of the yokes is a coil extending in a plane substantially parallel to the horizontal plane of the first legs extending distally from the loops. The coil is circular and comprises a distal bight portion extending proximately and arcuately at each end to define vertically-superimposed upper and lower substantially horizontal half-loops, each of which half-loops extend distally to the inner, lower extent of each yoke. The dimensions of the clip, in conjunction with the diameter and heat treat of the stainless steel wire, are selected to provide the appropriate desired spring force for the clip to occlude a vessel of a selected diameter range and physical properties.

In a first alternative embodiment of the invention, the vascular occluder comprises a resilient clip structure of stainless steel wire comprising a base from which extend two legs, the proximal portions of which extend in substantially mutually parallel relationship and substantially perpendicular to the base, while the medial portions of the legs extend angularly toward each other in substantially the same plane as the proximal portions and cross in superimposed or overlapping relationship proximate the juncture between the medial and distal portions of the legs. The distal portions of the legs initially extend from the medial portions in close, mutually parallel relationship and in substantially the same plane as the medial portions, and then bend or turn to one side substantially perpendicular to the plane of the base and proximal and medial portions of the legs, the bent free ends of the distal portions of the legs comprising vessel clamping elements and terminating in trocar points. A continuous ABS plastic sleeve, preferably blue, is molded over the base, proximal ends and juncture between the proximal and medial portions of the legs, the sleeve having two integral gripping pads of arcuate perimeter configuration extending from the proximal portions of the legs perpendicular to the base and opposite in direction from the free ends of the distal leg portions. As with the preferred embodiment, the dimensions of the clip, in conjunction with the diameter and heat treat of the stainless steel wire and also, in this case, the mechanical properties and thickness of the ABS sleeve are selected to provide the appropriate desired spring force.

A second alternative embodiment of the invention is similar in appearance to the first alternative embodiment, but the legs are hinged together as they cross between the proximal and medial portions, the spring force for the clip being provided by a coil or other spring structure interposed between the distal portions of the legs, there being no rigid base extending therebetween.

When compressed via inwardly directed pressure on the gripping loops or pads to separate the vessel clamping elements at the distal ends of the legs, and then applied and released to occlude the coronary artery during performance of the coronary anastomosis, the vascular occluder clip of the present invention readily penetrates the fat pad on the exterior of the heart due to the presence of the trocar tips on the clamping elements, and trauma to the artery is avoided by application of the clip in an indirect manner rather than directly on the coronary artery wall, so that a few millimeters of adjacent fat and myocardium are left on each side of the of the coronary artery to provide a cushion during occlusion. In such a manner, the artery is quickly and atraumatically occluded by the clamping elements at the distal ends of the clip legs, the remainder of the clip lying in place closely against the surface of the heart in a non-obstructive manner with the gripping loops or pads protruding for easy removal of the clip when desired. The arcuate configuration of the gripping loops or pads prevents snagging during the remainder of the surgical procedure. The clip may be removed by recompression thereof via the gripping loops or pads to release the distal leg end clamping elements from the artery, and lifted from the heart.

BRIEF DESCRIPTION OF THE DRAWINGS

The present invention will be more fully understood by one of ordinary skill in the art through a review of the following detailed description of the illustrated embodiments in the accompanying drawings, wherein.

DETAILED DESCRIPTION OF THE EMBODIMENTS OF THE INVENTION

Figure 1:
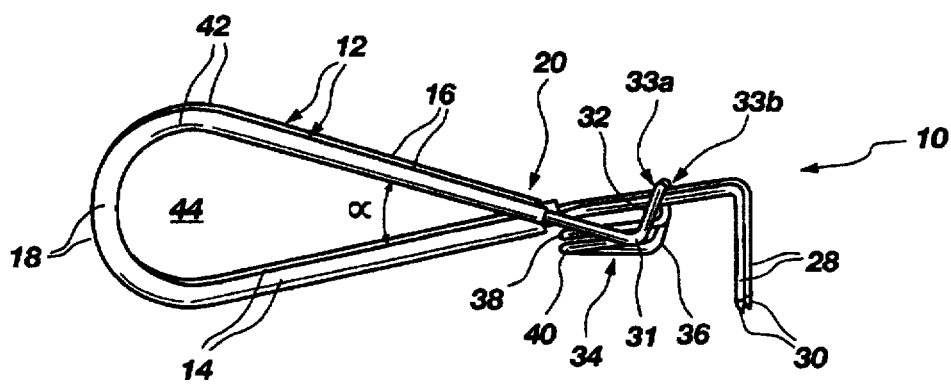
FIG. 1 comprises a side elevation of a preferred embodiment of the vascular occluder clip of the present invention.
Figure 2:
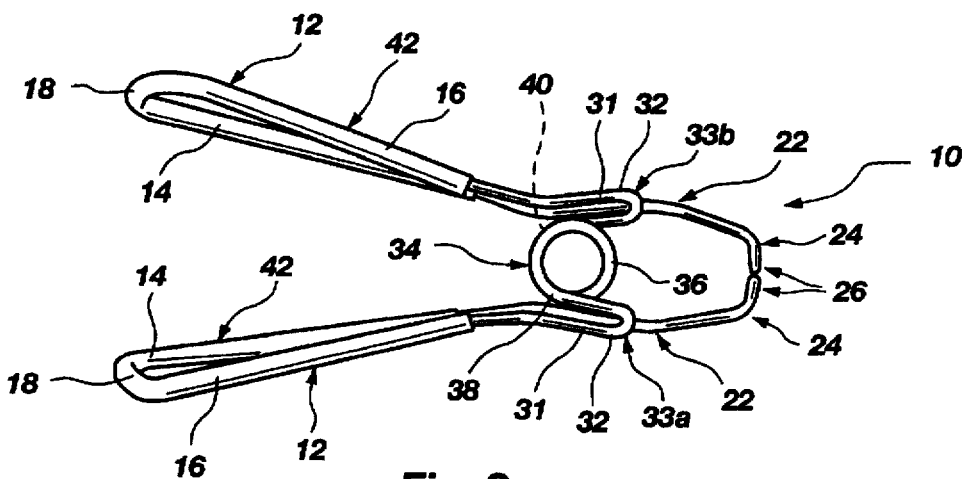
FIG. 2 comprises a top elevation of the preferred embodiment of the vascular occluder clip depicted in FIG. 1.

FIGS. 1 and 2 of the drawings depict a first preferred embodiment 10 of the vascular occluder clip of the present invention. Clip 10 includes two horizontally-extending gripping loops 12 at the proximal end thereof. Each loop 12 includes a first lower leg 14 and a second upper leg 16 converging distally from a proximally-located bight 18. Legs 14 and 16 of each loop 12 converge at an acute angle $\alpha$, crossing or overlapping at point 20 to close the distal end of each loop 12. The two loops 12 are divergent in a proximal direction, and lie in slightly off-vertical planes (see FIG. 2) which diverge or open as they extend upwardly in each loop plane.

The first, lower leg 14 of each loop 12 extends slightly inwardly of second, upper leg 16, and extends distally after crossing the second leg 16, remaining in substantially the same plane and in substantially parallel relationship to the other distally-extending first leg 14. First legs 14 may actually each diverge and then converge at a slight angle on each side of a point 22, before turning sharply inwardly toward each other at elbow 24 and then downwardly at elbow 26 in substantially parallel relationship and perpendicular to the plane of the remainder of the legs 14 between point 20 and elbow 26. The downwardly oriented segments 28 of the first legs 14 define vessel clamping elements, which terminate at points 30, which are preferably triangular or trocar points. If desired, segments 28 may be bowed gently outwardly to better grip a vessel when closed therearound.

The second, upper legs 16 of each loop 12 are bent upwardly at 31 with respect to the plane in which first legs 14 lie after crossing the first legs 14 at points 20 to close the loops 12. These upwardly-extending leg portions 32 are bent over and inwardly, then downwardly, to form yokes 33a and 33b enveloping legs 14 of the same loop 12 extending therethrough. At the inner, lower extents of the yokes 33a and 33b is a spring coil 34 lying in a plane generally parallel to the horizontal plane of legs 14 between point 20 and elbow 26. The coil 34 is substantially circular and includes a distal bight portion 36 which extends proximally and arcuately in overlapping relationship to form vertically-superimposed upper and lower half-loops 38 and 40. Each of these half-loops 38 and 40 then extends distally to the inner, lower end of a respective yoke 33a and 33b.

Coil 34 provides a resilient, controlled biasing force for downwardly-oriented first leg segments 28 for clamping of a vessel. The extended gripping loops 12 provide leverage for the user, while ensuring sensitivity to the touch and a degree of flexibility during compression of the loops 12 before the leg segments 28 are separated. The same flexibility ensures a gentle, gradual release of leg segments 28 about a vessel.

It be preferred that the wire from which clip 10 is formed of 302 stainless steel spring tempered wire of thirty-seven thousandths (0.037) inch diameter. It is also preferred that the wire loops 12 of clip 10 be covered with tubular sleeves 42 of plastic, preferably polyurethane, to provide a larger surface area for grasping and a higher coefficient of friction than bare metal to reduce slippage between the user's fingers and the loops 12. The heat treat of the wire may be adjusted to arrive at the desired spring force.

It is also contemplated that wire material, wire diameter, coil diameter, number of loops in the coil and the preload applied to the coil may be adjusted individually or in any combination to vary the spring force.

FIGS. 3–6 depict vascular occluder clip 10 in use.

Figure 3:
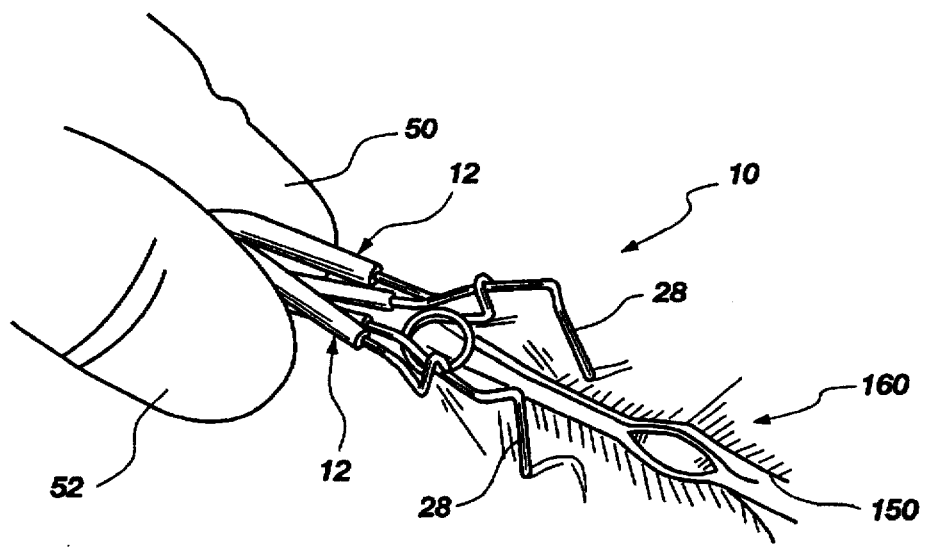
FIG. 3 depicts the vascular occluder clip of FIGS. 1 and 2 in the open mode being applied to a coronary artery.

FIG. 3 shows the thumb 50 and finger 52 of a user grasping and compressing loops 12 to open or separate leg segments 28, which are then pressed downwardly in the direction of the arrows into the fat pad 160 of the underlying organ on each side of vessel 150 to be occluded.

Figure 4:
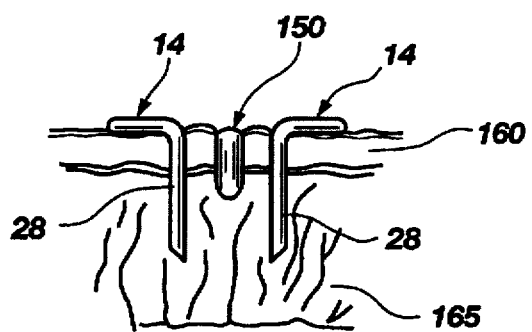
FIG. 4 depicts the clamping elements of the vascular occluder clip of FIGS. 1 and 2 in released, closed mode occluding an artery.

FIG. 4 depicts downwardly-extending leg segments 28 clamping a vessel 150 with fat pad 160 and underlying myocardium 165. Thus, potential damage to the septal perforators under the left anterior descending (LAD) is avoided because legs 28 substantially parallel vessel 150 rather than surrounding it.

Figure 5:
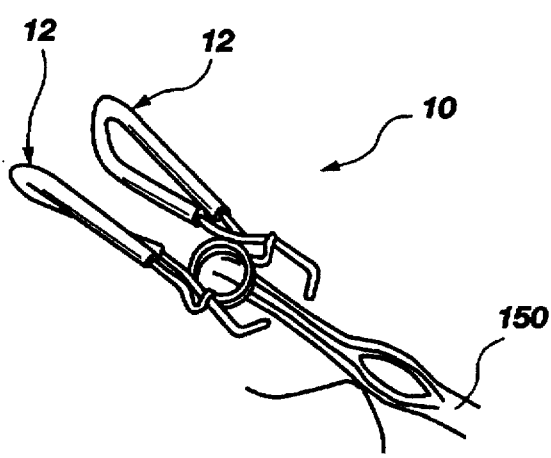
FIG. 5 depicts the vascular occluder clip of FIGS. 1 and 2 occluding the arteriotomy segment during antegrade cardioplegia.

FIG. 5 depicts occlusion by a clip 10 of the arteriotomy segment during antegrade cardioplegia and/or blood. Thus, myocardial protection during anastomosis is optimized.

Figure 6:
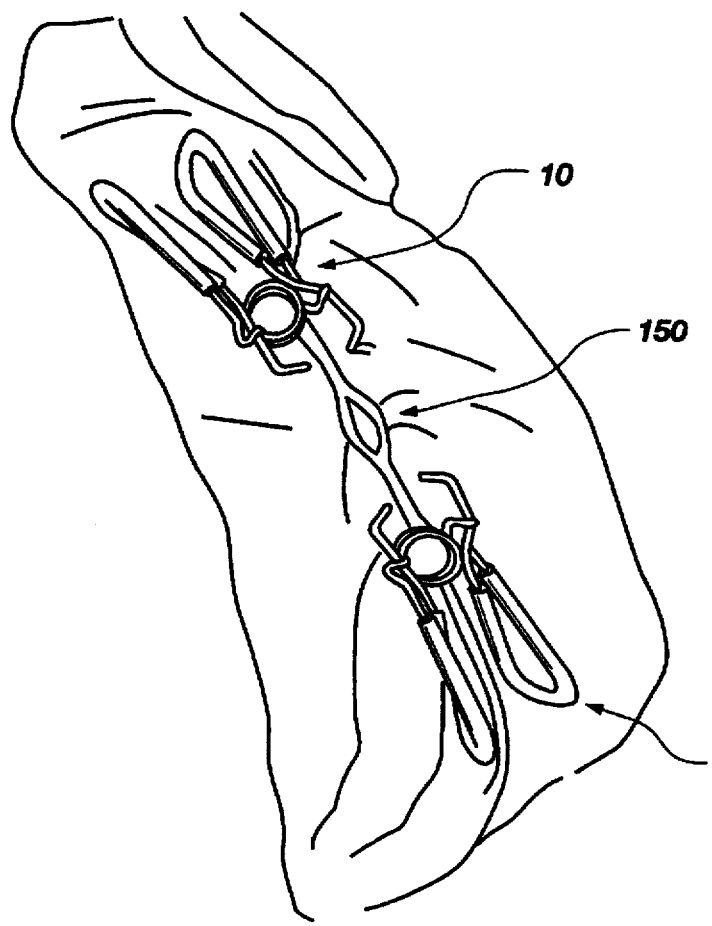
FIG. 6 depicts a plurality of vascular occluder clips of FIGS. 1 and 2 applied to a vessel on each side of an incision for superior surgical site visualization.

FIG. 6 depicts a plurality of clips 10 arranged to occlude a vessel 150 for enhanced surgical site visualization without the need for additional blood clearing devices.

The vascular occluder clip of the present invention has application to both continuous and intermittent antegrade/retrograde cardioplegia, as well as coronary bypass procedures performed without cardiopulmonary bypass.

Application of vascular occluder clips 10 to a vessel is extremely simple. Loops 12 are grasped by the fingertips of the user as shown in FIG. 3, loop 12 then being compressed toward each other. The slight outward "tilt" of the loops enhances the user's grip, as does the open areas 44 within each loop 12, which accommodates the pads of the user's fingertips. After loops 12 are compressed, which separates or opens leg segments 28 against the spring force of coil 34, leg segments 28 are pressed straight down into the fat pad 160 and myocardin 165 on either side of the target vessel 150. Trocar points 30 facilitate penetration substantially without trauma. After leg segments have penetrated as far as possible, loops 12 are released and leg segments 28 act as clamping elements to occlude target vessel 150 as shown in FIG. 4. Removal of clip 10 is accomplished by grasping and compressing loops 12 to separate leg segments 28 and release vessel 150, after which slip 10 is moved straight upwardly parallel to the orientation of leg segments 28. It should be noted, as shown in FIGS. 5 and 6, that the protected location of coil 34 and the long, low-profile loops 12 minimize snagging by tubes, suture thread and surgical implements employed in the operating theatre.

Figure 7:
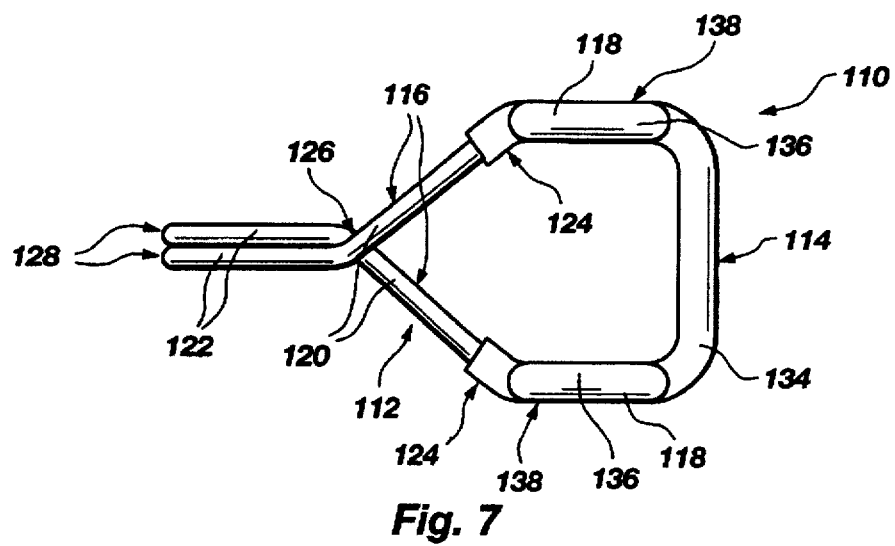
FIG. 7 comprises a top elevation of an alternative embodiment of the vascular occluder clip of the present invention.
Figure 8:
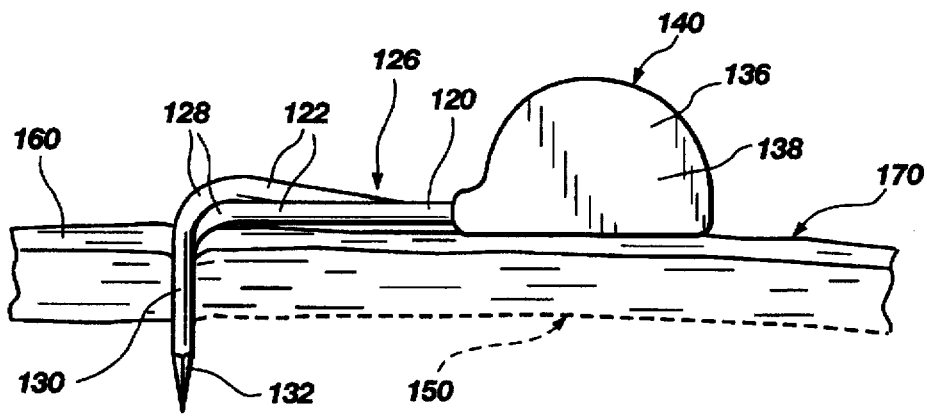
FIG. 8 comprises a side elevation of the alternative embodiment of FIG. 7 as applied to occlude a coronary artery.

Referring now to FIGS. 7 and 8 of the drawings, a first alternative embodiment of the vascular occluder clip 110 of the present invention comprises a 316 stainless steel spring tempered wire 112 including a base 114 having first and second legs 116 extending therefrom. Each leg has a proximal potion 118, a medial potion 120, and a distal potion 122. The proximal potions of the legs 116 extend substantially perpendicular to the base 114 and in a substantially mutually parallel relationship, while the medial portions 120 turn inwardly at elbows 124 toward each other at approximately 45° angles to the proximal potions 118 and remain in substantially the same plane, crossing in overlapping or superimposed relationship at 126, whereafter the distal potions 122 of legs 116 again extend in mutually parallel relationship and in close mutual proximity when clip 112 is uncompressed and in a completely closed state as depicted in FIG. 7. Distal potions 122 are bent at 128 at approximately a right angle to the plane of the base 114 and the proximal and medial portions 118 and 120, extending away therefrom to distal ends 130 defining clamping elements terminating at triangular, or trocar, points 132.

A sleeve 134 of ABS plastic, preferably blue, is molded over the base 114, proximal leg potions 118 and junctures 124. The sleeve 134 includes integral gripping pads 136 which extend from sleeve 134 at the proximal portions 118 of legs 116 perpendicular to the plane of base 114 and proximal and medial leg portions 118 and 120, and opposite in direction to free ends 130 of distal leg potion 122. The gripping pads 136 may be smooth or have a grooved or toughened exterior surface at 138 to facilitate gripping by the fingers or preferably by a clamp to compress clip 110 and thereby move distal ends 130 of legs 116 apart for placement on either side of a vessel to effect the desired occlusion by subsequent release of the clip. The gripping pads 136 preferably include an arcuate perimeter 140 to avoid snagging, as will be more fully explained hereafter.

In order to provide adequate but not excessive spring force for clip 110 to effect occlusion of a vessel, the diameter and temper or heat treat of stainless steel wire 112 and the thickness and material properties of sleeve 134 are carefully selected to provide, in combination, the desired spring force for the completed device. Such selection and combination of desired parameters being well within the abilities of those of ordinary skill in the art, no detailed description of the process is believed to be necessary.

When the alternate vascular occluder clip 110 of the present invention is applied to occlude, for example, a coronary artery 150 (see FIG. 8), the clip 110 is compressed via inwardly-directed pressure applied manually or via a clamp to gripping pads 136 to move distal ends 130 of legs 116 away from each other a distance substantially greater than the diameter of the artery 150 to be occluded. Distal ends 130 are then caused to enter and penetrate the fat pad 160 of the heart 170, such penetration being facilitated by the trocar points 132. Distal ends 130 are caused, prior to penetration, to separate a sufficient distance to enable clip 110 to grip a few millimeters of fat pad 160 of the heart 170 on each side of the artery 150 to cushion the effect of the clip 110 when it is released to clamp free ends 130 on the artery 150, thus avoiding trauma thereto. It should be noted, as depicted in FIG. 8, that clip 110, after application, lies in close proximity against the heart 170, the only substantial protrusion from clip 110 from the surface of heart 170 being gripping pads 136, the arcuate perimeters 140 thereof presenting smooth edges which are not easily snagged by tubes, suture thread, and surgical implements employed by the surgical team in the performance of the remainder of the procedure. Clip 110 is removed from the artery 150 by recompression via gripping pads 136 to separate distal leg ends 130, and lifted from the heart.

Figure 9:
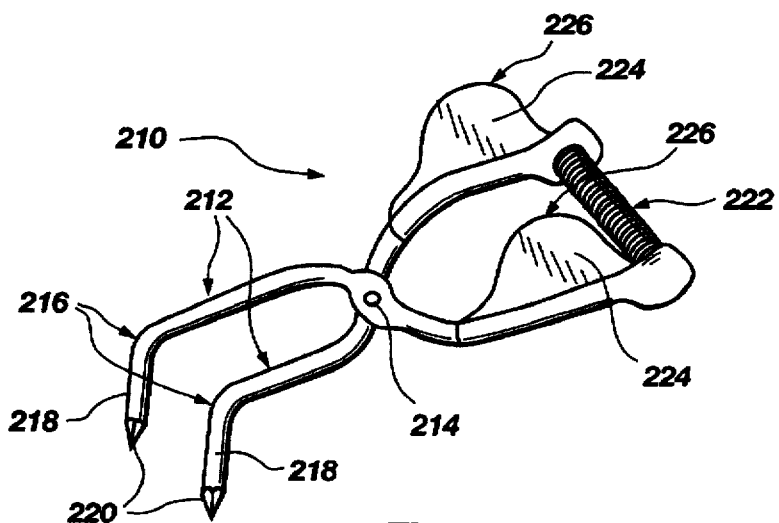
FIG. 9 comprises a perspective view of a second alternative embodiment of the vascular occluder clip of the present invention.

Referring now to FIG. 9, a second alternative embodiment 210 of the vascular occluder clip of the present invention will be described. Clip 210 comprises first and second legs 212, hinged at 214 for a scissor-like action. As with the preferred embodiment, legs 212 lie primarily in a single plane, and each bends or turns at a right angle at 216 to extend to distal ends 218 comprising clamping elements terminating at trocar points 220. In lieu of using the inherent spring force of tempered wire as in the preferred and first alternative embodiments, clip 210 is provided with a discrete coil spring 222 which extends between the proximal ends of legs 212, being maintained therebetween by protrusions (not shown) which extend from legs 212 into the ends of spring 222. Gripping pads 224 of arcuate perimeter 226 are molded onto legs 212 between the hinge point 214 and the connections to spring 222, extending perpendicularly to the major plane of legs 212. Application of clip 210 to the vessel and removal therefrom is effected in the same manner as with clips 10 and 110, and so will not be described.

It should be understood that, while application of the vascular occluder of the present invention has been described primarily with respect to coronary anastomosis, the invention is not so limited. It is contemplated that the present invention has utility in many other procedures requiring rapid, positive external vascular occlusion, including without limitation trauma management for rapid occlusion of "bleeders" or severed or damaged vessels without preliminary surgical intervention.

While the present invention has been described in terms of exemplary preferred and alternative embodiments, it will be readily understood and appreciated by one of ordinary skill in the art that it is not so limited, and that many additions, deletions and modifications to the preferred embodiments may be made within the scope of the invention as hereinafter claimed.

What is claimed is:

1. An apparatus for occluding a blood vessel, comprising:
   first and second longitudinally extending members formed from a single piece of wire, said members each including proximal and distal portions, said proximal portions being mutually laterally separated;
   said distal portions of each of said members having substantially mutually parallel, substantially linear, pointed distal ends extending substantially transversely to said distal portions of said members;
   means formed from said single piece of wire for resiliently biasing said distal ends of said members into close mutual proximity; and
   means for gripping each of said members on the proximal portions thereof, said means for gripping extending transversely to said longitudinal members to one side thereof opposite in direction to said distal ends of said distal member portions.

2. The apparatus of claim 1, further including a base extending between said proximal portions of each of said members, said base and said members being formed of resilient wire, and wherein said means for resiliently biasing comprises said base and said proximal portions of said members.

3. The apparatus of claim 2, wherein said members each further include medial portions, said members cross in superimposed relationship proximate the juncture of said medial and distal portions, and said distal portions of said members proximate said juncture lie in close mutual proximity.

4. The apparatus of claim 3, wherein said pointed distal ends comprise trocar points.

5. The apparatus of claim 1, wherein said means for gripping comprise pads affixed to said members.

6. The apparatus of claim 5, wherein said pads extend from integral sleeves surrounding a portion of each of said members.

7. The apparatus of claim 2, wherein said means for gripping comprise pads affixed to said proximal portions of said members.

8. The apparatus of claim 7, wherein said pads extend from an integral sleeve surrounding said base and at least part of said proximal portions of each of said members.

9. The apparatus of claim 8, wherein said integral sleeve and pads are formed of plastic, and said means for resiliently biasing further comprises said plastic sleeve in combination with said base and proximal portions of said members.

10. The apparatus of claim 1, wherein said means for gripping are planar and of arcuate profile.

11. The apparatus of claim 10, wherein said planar gripping means are of semicircular profile.

12. The apparatus of claim 1, wherein said means for gripping comprise gripping loops each defined by a loop of wire, said gripping loops diverging from one another as they extend proximally.

13. The apparatus of claim 12, further including tubular plastic sleeves enveloping said wire of said gripping loops throughout a major extent thereof.

14. The apparatus of claim 12, wherein said gripping loops tilt slightly laterally outwardly from bottom to top thereof.

15. The apparatus of claim 1, wherein said biasing means comprises a spring also formed from said single piece of wire and located between said two members.

16. The apparatus of claim 15, wherein said spring comprises a coil spring having at least one 360° coil loop, said at least one coil loop oriented substantially parallel to said members.

17. The apparatus of claim 15, wherein said gripping means comprise a wire loop on each of said members, said wire loops each having a proximal bight portion and first and second legs extending distally and crossing at an acute angle to close said loop.

18. The apparatus of claim 17, wherein said first legs are lower than said second legs prior to said crossing, and extend distally thereafter, said first legs then turn transversely laterally inwardly and then extend downwardly in a mutually parallel relationship, said downward extent of said first legs comprising said clamping elements.

19. The apparatus of claim 18, wherein said second legs define, distally of said crossing, transversely-extending yokes through which said distally extending first legs of the same member pass between said crossings and said transverse laterally inward turns of said first legs.

20. The apparatus of claim 19, wherein said second legs extend proximally from the inner ends of said yokes into said coil spring.

21. The apparatus of claim 20, wherein said coil spring comprises one 360° coil loop having first and second vertically overlapped or superimposed ends at the proximal end of said coil, said superimposed ends comprising approximately 180° arcs into which said second legs extend proximally from said yokes.

22. The apparatus of claim 19, wherein said first legs extend slightly laterally outwardly between said crossings and the points at which said first legs pass through said yokes, and then turn slightly laterally inwardly to the points at which the first legs turn transversely laterally inwardly.

23. The apparatus of claim 1, wherein said pointed distal ends comprise trocar points.

* * * * *

UNITED STATES PATENT AND TRADEMARK OFFICE
CERTIFICATE OF CORRECTION

PATENT NO.  : 5,683,405  
DATED       : Nov. 4, 1997  
INVENTOR(S) : Yacoubian et al.

Page 1 of 2

It is certified that error appears in the above-indentified patent and that said Letters Patent is hereby corrected as shown below:

| | |
|---|---|
| On the Title Page | Under "Other Publications", line 7 - change "Produc" to --Product-- |
| In Col. 1, line 2 | Change "OFT HE" to --OF THE-- |
| In Col. 1, line 20 | change "Bunt, et at," to --Bunt, et al,-- |
| In Col. 3, line 3 | change "afso" to --also-- |
| In Col. 3, line 24 | after "the" delete --of the-- |
| In Col. 4, line 51 | change "be" to --is-- |
| In Col. 4, line 52 | before "of 302" insert --be-- |
| In Col. 5, line 28 | change "myocardin" to --myocardium-- |
| In Col. 5, line 30 | after "leg segments" insert --28-- |
| In Col. 5, line 35 | change "slip" to --clip-- |
| In Col. 5, line 47 | change "potion" to --portion-- (all 3 occurrences) |
| In Col. 5, line 48 | change "potions" to --portions-- |
| In Col. 5, line 52 | change "potions" to --portions-- |
| In Col. 5, line 55 | change "potions" to --portions-- |
| In Col. 5, line 56 | change "clip 112" to --clip 110-- |
| In Col. 5, line 58 | change "potions" to --portions-- |
| In Col. 5, line 62 | after "points 132" insert --(FIG. 8)-- |

UNITED STATES PATENT AND TRADEMARK OFFICE
CERTIFICATE OF CORRECTION

PATENT NO. : 5,683,405
DATED : Nov. 4, 1997
INVENTOR(S) : Yacoubian et al.

It is certified that error appears in the above-indentified patent and that said Letters Patent is hereby corrected as shown below:

| | |
|---|---|
| In Col. 5, line 64 | change "potions" to --portions-- |
| In Col. 6, line 2 | change "free ends 130" to --distal ends 130--; change "potion" to --portion-- |
| In Col. 6, line 4 | change "toughened" to --roughened-- |
| In Col. 6, line 33 | change " free ends 130" to --distal ends 130-- |
| In Col. 8, line 39 | change " crossings" to --crossing-- |
| In Col. 8, line 51 | change " crossings" to --crossing-- |
| In Col. 7, line 20 | after "substantially" and before "linear" delete --,-- (comma) |

Signed and Sealed this

Fourteenth Day of April, 1998

*Attest:*

BRUCE LEHMAN

*Attesting Officer*    Commissioner of Patents and Trademarks